United States Patent
Hinshaw

(10) Patent No.: US 6,398,794 B1
(45) Date of Patent: Jun. 4, 2002

(54) SPLINTER REMOVAL DEVICE

(76) Inventor: Eldon J. Hinshaw, 1515 Six Points Rd., Bloomington, IL (US) 61701

( * ) Notice: Subject to any disclaimer, the term of this patent is extended or adjusted under 35 U.S.C. 154(b) by 68 days.

(21) Appl. No.: 09/714,910

(22) Filed: Nov. 17, 2000

(51) Int. Cl.[7] .......................... A61B 17/50; B65D 69/00
(52) U.S. Cl. ...................................... 606/131; 206/570
(58) Field of Search ................... 606/131, 167, 606/181, 183; 206/570, 803; 30/353

(56) References Cited

U.S. PATENT DOCUMENTS

| | | |
|---|---|---|
| 172,868 A | 2/1876 | Clough |
| D21,761 S | 8/1892 | Puddefoot |
| 2,451,994 A | 10/1948 | Towns |
| 2,803,252 A * | 8/1957 | Bloome |
| 3,971,386 A | 7/1976 | Yamada |
| 4,401,434 A | 8/1983 | Harris |
| 4,589,178 A * | 5/1986 | Staffeld |
| 5,197,482 A | 3/1993 | Rank et al. |
| 5,334,195 A * | 8/1994 | Gollobin |

* cited by examiner

*Primary Examiner*—Jeffrey A. Smith

(57) ABSTRACT

A splinter removal tool for removing splinters imbedded in the skin. The splinter removal tool includes a panel. The panel is elongate and has generally planar top side and a generally planar bottom side. The panel has a first end edge, a second end edge, a first side edge and a second side edge. The first end edge tapers to a point. The panel is generally divided into a first half and a second half such that the first half abuts the first end. The first half is twisted such that the first side edge and the second side edge simultaneously define a helix extending around a longitudinal axis of the panel. The panel comprises a substantially rigid material.

7 Claims, 3 Drawing Sheets

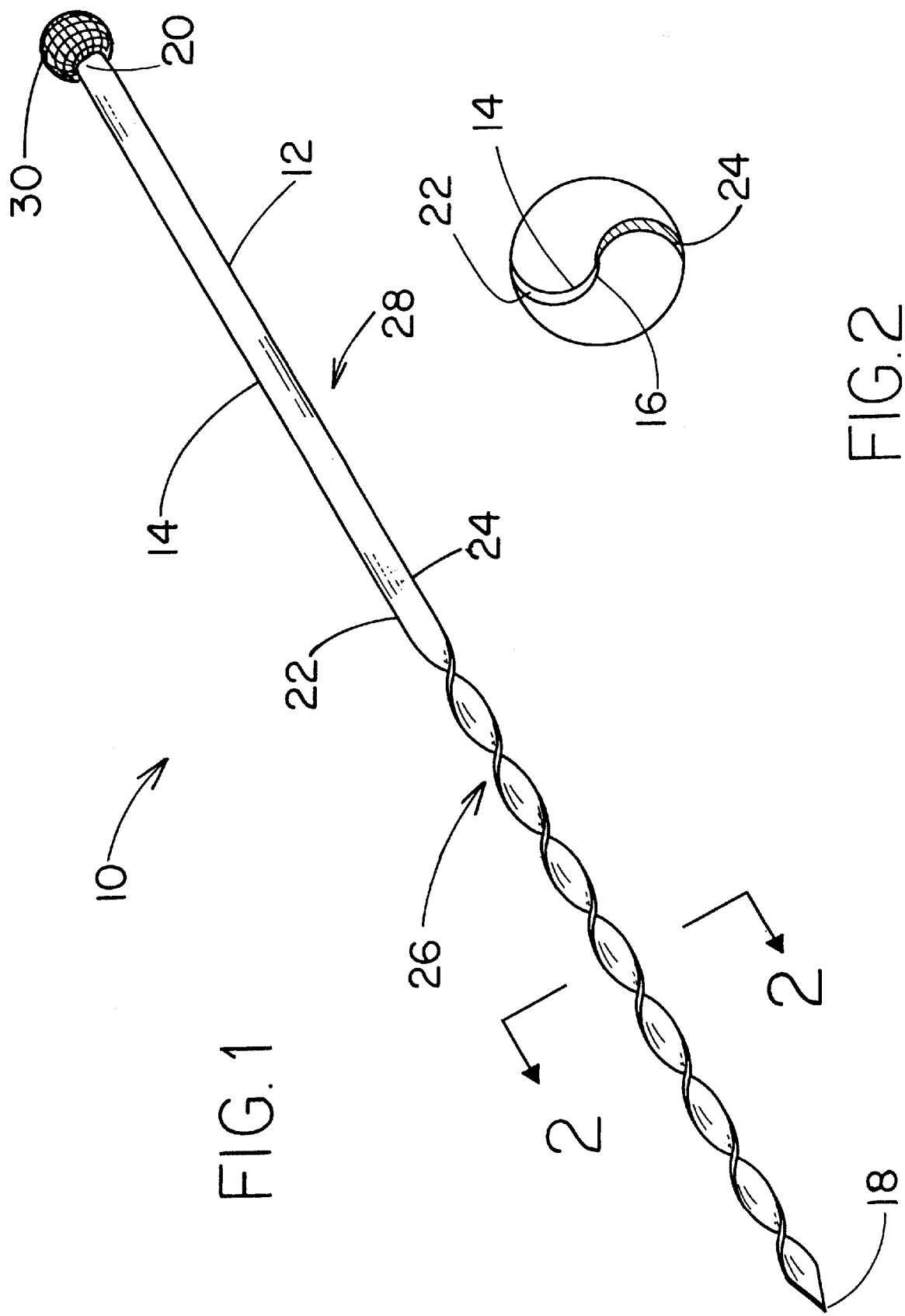

SPLINTER REMOVAL DEVICE

BACKGROUND OF THE INVENTION

1. Field of the Invention

The present invention relates to splinter removal tools and more particularly pertains to a new splinter removal tool for removing splinters imbedded in the skin.

2. Description of the Prior Art

The use of splinter removal tools is known in the prior art. More specifically, splinter removal tools heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 4,401,434; 2,451,994; 3,971,386; 5,197,482; 172,868; and U.S. Des. Pat. No. 21,761.

While these devices fulfill their respective, particular objectives and requirements, the aforementioned patents do not disclose a new splinter removal tool. The inventive device includes a panel. The panel is elongate and has generally planar top side and a generally planar bottom side. The panel has a first end edge, a second end edge, a first side edge and a second side edge. The first end edge tapers to a point. The panel is generally divided into a first half and a second half such that the first half abuts the first end. The first half is twisted such that the first side edge and the second side edge simultaneously define a helix extending around a longitudinal axis of the panel. The panel comprises a substantially rigid material.

In these respects, the splinter removal tool according to the present invention substantially departs from the conventional concepts and designs of the prior art, and in so doing provides an apparatus primarily developed for the purpose of removing splinters imbedded in the skin.

SUMMARY OF THE INVENTION

In view of the foregoing disadvantages inherent in the known types of splinter removal tools now present in the prior art, the present invention provides a new splinter removal tool construction wherein the same can be utilized for removing splinters imbedded in the skin.

The general purpose of the present invention, which will be described subsequently in greater detail, is to provide a new splinter removal tool apparatus and method which has many of the advantages of the splinter removal tools mentioned heretofore and many novel features that result in a new splinter removal tool which is not anticipated, rendered obvious, suggested, or even implied by any of the prior art splinter removal tools, either alone or in any combination thereof.

To attain this, the present invention generally comprises a panel. The panel is elongate and has generally planar top side and a generally planar bottom side. The panel has a first end edge, a second end edge, a first side edge and a second side edge. The first end edge tapers to a point. The panel is generally divided into a first half and a second half such that the first half abuts the first end. The first half is twisted such that the first side edge and the second side edge simultaneously define a helix extending around a longitudinal axis of the panel. The panel comprises a substantially rigid material.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new splinter removal tool apparatus and method which has many of the advantages of the splinter removal tools mentioned heretofore and many novel features that result in a new splinter removal tool which is not anticipated, rendered obvious, suggested, or even implied by any of the prior art splinter removal tools, either alone or in any combination thereof.

It is another object of the present invention to provide a new splinter removal tool which may be easily and efficiently manufactured and marketed.

It is a further object of the present invention to provide a new splinter removal tool which is of a durable and reliable construction.

An even further object of the present invention is to provide a new splinter removal tool which is susceptible of a low cost of manufacture with regard to both materials and labor, and which accordingly is then susceptible of low prices of sale to the consuming public, thereby making such splinter removal tool economically available to the buying public.

Still yet another object of the present invention is to provide a new splinter removal tool which provides in the apparatuses and methods of the prior art some of the advantages thereof, while simultaneously overcoming some of the disadvantages normally associated therewith.

Still another object of the present invention is to provide a new splinter removal tool for removing splinters imbedded in the skin.

Yet another object of the present invention is to provide a new splinter removal tool which includes a panel. The panel is elongate and has generally planar top side and a generally planar bottom side. The panel has a first end edge, a second end edge, a first side edge and a second side edge. The first end edge tapers to a point. The panel is generally divided into a first half and a second half such that the first half abuts the first end. The first half is twisted such that the first side edge and the second side edge simultaneously define a helix extending around a longitudinal axis of the panel. The panel comprises a substantially rigid material.

Still yet another object of the present invention is to provide a new splinter removal tool that is easily positioned in the hole of the splinter and turned to bias, or pull, the splinter out of the hole when the device is turned.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a schematic side view of a new splinter removal tool according to the present invention.

FIG. 2 is a schematic cross-sectional view taken along line 2—2 of the present invention.

DESCRIPTION OF THE PREFERRED EMBODIMENT

Figure 3:
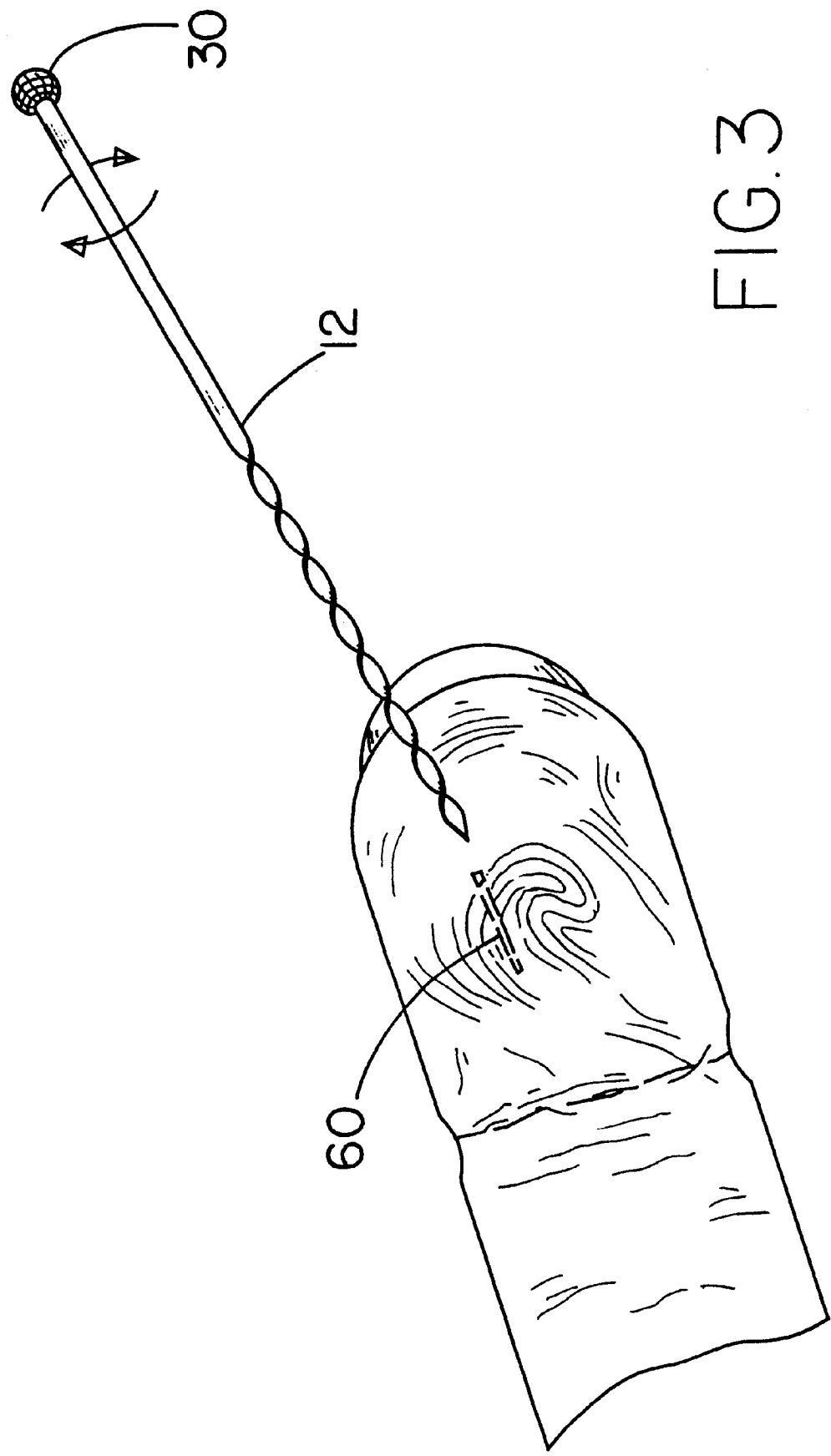
FIG. 3 is a schematic in-use view of the present invention.
Figure 4:
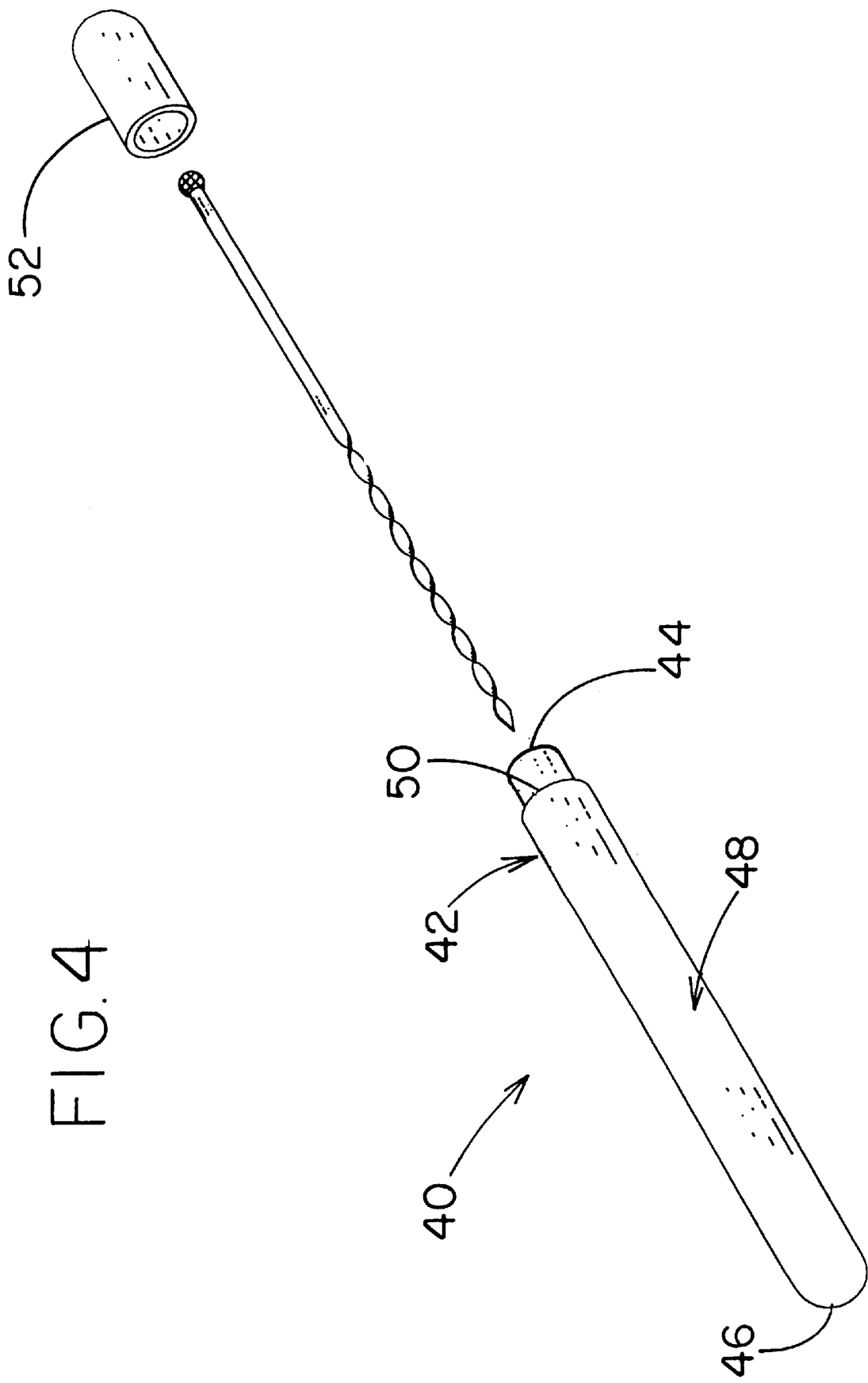
FIG. 4 is a schematic side view of the present invention.

With reference now to the drawings, and in particular to FIGS. 1 through 4 thereof, a new splinter removal tool embodying the principles and concepts of the present invention and generally designated by the reference numeral 10 will be described.

As best illustrated in FIGS. 1 through 4, the splinter removal tool 10 generally comprises a panel 12. The panel 12 is elongate and has generally planar top side 14 and a generally planar bottom side 16. The panel 12 has a first end edge 18, a second end edge 20, a first side edge 22 and a second side edge 24. The first end edge 18 tapers to a point. The panel 12 is generally divided into a first half 26 and a second half 28 such that the first half abuts the first end edge 18. The first half 26 is twisted such that the first side edge 22 and the second side edge 24 each simultaneously define a helix extending around a longitudinal axis of the panel 12, or, in other words, together define a double helix. The panel 12 comprises a substantially rigid material. The rigid material is ideally a metal. The panel 12 preferably has length generally between 3 inches and 5 inches, and ideally a length equal to 4¼ inches. The panel 12 has a width generally between ¹⁄₁₆ inches and ⅛ inches and ideally a width equal to ³⁄₁₆ inches. A cross-section of the first half taken perpendicular to the longitudinal axis has an angle of twist generally between 15 degrees and 25 degrees, and ideally equal to 20 degrees.

A gripping member 30 for gripping the panel 12 is integrally coupled to the second end edge 20 of the panel 12. The gripping member 30 comprises a sphere having a knurled surface.

A carrying case 40 for the plate 12 includes a tubular member 42 having an open end 44, a closed end 46 and a peripheral wall 48 extending therebetween. The tubular member 42 is generally hollow. The plate 12 may be extended into the open end 44. The peripheral wall 48 has a peripheral shoulder 50 therein. The peripheral shoulder 50 is positioned generally adjacent to the open end 44. A cap member 52 has a size and shape adapted for removably positioning over the open end and abutting the peripheral shoulder 50. The cap member 52 is attached to the tubular member 42 by friction.

In use, the device is used to remove a splinter 60 lodged in a person's skin. The first end edge 18 of the plate 12 is inserted in the hole created by the splinter 60. The plate 12 is turned when it is abutting the splinter 60. The curved side edges of the plate grip the splinter and the plate is turned to remove the splinter, which will ride up plate as it is turned.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A splinter removal device, said device comprising:
   a panel, said panel being elongate and having a generally planar top side and a generally planar bottom side, said panel having a first end edge, a second end edge, a first side edge and a second side edge, said first end edge tapering to a point, said panel being generally divided into a first half and a second half such that said first half abuts said first end, said first half being twisted such that said first side edge and said second side edge simultaneously define a helix extending around a longitudinal axis of said panel, said panel comprising a substantially rigid material.

2. The splinter removal device as in claim 1, wherein said panel further comprises:
   said panel having a length generally between 3 inches and 5 inches and a width generally between ¹⁄₁₆ inches and ⅛ inches.

3. The splinter removal device as in claim 1, wherein said panel further comprises:
   a cross-section of said first half taken perpendicular to said longitudinal axis having an angle of twist generally between 15 degrees and 25 degrees.

4. The splinter removal device as in claim 1, further including:
   a gripping member for gripping said panel, said gripping member being integrally coupled to said second end edge of said panel, said gripping member comprising a sphere, said sphere having a knurled surface.

5. The splinter removal device as in claim 4, further including:
  a carrying case for said plate, said carrying case including;
    a tubular member having an open end, a closed end and a peripheral wall extending therebetween, said tubular member being generally hollow wherein said plate may be extended into said open end.

6. The splinter removal device as in claim 5, wherein said carrying case further includes:
  said peripheral wall of said tubular member having a peripheral shoulder therein, said peripheral shoulder being positioned generally adjacent to said open end; and
  a cap member, said cap member having a size and shape adapted for removably positioning over said open end and abutting said peripheral shoulder.

7. A splinter removal device, said device comprising:
  a panel, said panel being elongate and having a generally planar top side and a generally planar bottom side, said panel having a first end edge, a second end edge, a first side edge and a second side edge, said first end edge tapering to a point, said panel being generally divided into a first half and a second half such that said first half abuts said first end, said first half being twisted such that said first side edge and said second side edge simultaneously define a helix extending around a longitudinal axis of said panel, said panel comprising a substantially rigid material, said rigid material comprising a metal, said panel having a length generally between 3 inches and 5 inches, said panel having a width generally between $1/16$ inches and $1/8$ inches, a cross-section of said first half taken perpendicular to said longitudinal axis having an angle of twist generally between 15 degrees and 25 degrees;
  a gripping member for gripping said panel, said gripping member being integrally coupled to said second end edge of said panel, said gripping member comprising a sphere, said sphere having a knurled surface;
  a carrying case for said plate, said carrying case including;
    a tubular member having an open end, a closed end and a peripheral wall extending therebetween, said tubular member being generally hollow wherein said plate may be extended into said open end, said peripheral wall having a peripheral shoulder therein, said peripheral shoulder being positioned generally adjacent to said open end; and
    a cap member, said cap member having a size and shape adapted for removably positioning over said open end and abutting said peripheral shoulder.

* * * * *